United States Patent [19]
Lin

[11] Patent Number: 5,977,175
[45] Date of Patent: Nov. 2, 1999

[54] METHODS AND COMPOSITIONS FOR IMPROVING DIGESTION AND ABSORPTION IN THE SMALL INTESTINE

[75] Inventor: Henry C. Lin, Manhattan Beach, Calif.

[73] Assignee: Cedars-Sinai Medical Center, Los Angeles, Calif.

[21] Appl. No.: 08/832,307

[22] Filed: Apr. 3, 1997

Related U.S. Application Data

[63] Continuation of application No. 08/442,843, May 17, 1995, abandoned.

[51] Int. Cl.$^6$ .................................................... A61K 31/20
[52] U.S. Cl. ........................... 514/558; 424/457; 424/458; 424/489; 424/498; 514/549; 514/552; 514/560; 514/784; 514/785; 514/786
[58] Field of Search ..................................... 514/549, 552, 514/558, 560, 784, 785, 786; 424/457, 458, 489, 498

[56] References Cited

U.S. PATENT DOCUMENTS

| | | | |
|---|---|---|---|
| 4,160,452 | 7/1979 | Theeuwes | 128/260 |
| 4,183,960 | 1/1980 | Asher et al. | 424/365 |
| 4,193,985 | 3/1980 | Bechgaard et al. | 924/19 |
| 4,256,108 | 3/1981 | Theeuwes | 128/260 |
| 4,265,874 | 5/1981 | Bonsen et al. | 424/15 |
| 4,572,833 | 2/1986 | Pedersen et al. | 424/20 |
| 4,690,822 | 9/1987 | Uemura et al. | 424/455 |
| 4,863,744 | 9/1989 | Urquhart et al. | 424/484 |
| 5,322,697 | 6/1994 | Meyer | 424/458 |
| 5,411,751 | 5/1995 | Crissinger et al. | 426/2 |

FOREIGN PATENT DOCUMENTS

| | | |
|---|---|---|
| 0 200 902 A3 | 11/1986 | European Pat. Off. . |
| 0 539 319 A2 | 4/1993 | European Pat. Off. . |

OTHER PUBLICATIONS

XP 00613253 Brown, N. J. et al., "Characteristics of lipid–substances activating the ileal brake in the rat", Sub–Department of Gastrointestinal Physiology and Nutrition, Department of Biomedical Science, University of Sheffield, Western Bank, Sheffield, pp. 1126–1129, accepted for publication Dec. 4, 1989.
Schemann, M. et al., "Postprandial Patterns of Canine Jejunal Motility and Transit of Luminal Content", Gastroenterology 90(4): 991–1000 (1996).
Muranishi, S. et al., Potential Absorption of Heparin from the Small Intestine and the Large Intestine inthe Presence of Monoolein Mixed Micelles, Chem. Pharm. Bull. 25(5): 1159–1161 (1977).
Starha et al, Cesk. Farm., 21(7), 311–14 (Abstract), 1972.
Minina et al, Khim.–Farm, ZH., 12(2), 120–5 (Abstract), 1978.
Anderson, et al. "Influence of infulsate viscosity on intestinal absorption in the rat," *Gastroenterology*, 97:938–943 (1989).
Booyse et al., "Effects of chronic oral consumption of nicotine on the rabbit aortic endothelium," *Am. J. of Pathology*, 102:229–238 (1981).

Brown and Goldstein, "The Hyperlipoproteinemias and Other Disorders of Lipid Metabolism," Chapter 103, Section 2, on "Disorders of intermediary metabolism", *Harrison's Principles of Internal Medicine*, 13th Ed, 2058–2069 (1994).
Brown, N. J., et al. "Characteristics of lipid substances activating the ileal brake in the rat," *Gut*, 31(10):1126–1129 (Oct. 1990).
Bühner, and Ehrlein, "Characteristics of Postprandial Duodenal Motor Patterns in Dogs," *Dig. Dis. Sci.*, 34:1873–1881 (1989).
Cammack et al., "Effect of prolonged exercise on the passage of a solid meal through the stomach and small intestine," *Gut*, 23::957–961 (1982).
Carlson et al., "Effects of Nicotine on Gastric, Antral and Duodenal Contractile Activity in the Dog," *J. Pharm. Exp. Ther.*, 172:367–376 (1970).
Cohn C., "Feeding patterns and some aspects of cholesterol metabolism," *Federation Proc.*, 23:76–81 (1964).
Cohn, C., "Meal–Eating, Nibbling and Body Metabolism," *J. Am. Dietet. Assoc.*, 38:433–436 (1961).
Davis et al., "The Effect of Density on the Gastric Emptying of Single–Multiple–Unit Dosage Forms," *Pharm. Res.*, 3:208–213 (1986).
Delin, et al., "Comparison of Gamma Camera and Withdrawal Methods for the Measurement of Gastric Emptying," *Scand. J. Gastroent*, 13:867–872 (1978).
Dreznik, Z., et al., "Effect of Ileal Oleate on Interdigestive Intestinal Motility of the Dog," *Dig. Dis. Sci.*, 39(7):1511–1518 (Jul. 1994).
Edes, et al., "Diarrhea in Tube–Fed Patients: Feeding Formula Not Necessarily the Cause," *Am. J. Clin. Nutr.*, 50:553–558 (1989).
Frankenfield and Beyer, "Soy–polysaccharide fiber: effect on diarrhea in tube–fed, head–injured patients," *Am. J. Clin. Nutr.*, 50:553–558 (1989).
Fraser, et al., "The Effect of Dietary Fat Load on the Size and Composition of Chylomicrons in Thoracic Duct Lymph," *Q. J. Exp. Physicol.*, 53:390–398 (1968).
Girardet and Benninghoff, "Surgical Techniques for Long–Term Study of Thoracic Duct Lymph Circulation in Dogs," *J. Surg. Res.*, 15:168–175 (1973).
Gwinup, et al., "Effect of Nibbling Versus Gorging on Serum Lipids in Man," *Am. J. Chin. Nutr.*, 13:209–213 (1963).

(List continued on next page.)

*Primary Examiner*—Richard L. Raymond
*Attorney, Agent, or Firm*—Pretty, Schroeder & Poplawski

[57] ABSTRACT

The present invention provides methods and compositions for slowing gastrointestinal transit and prolonging residence time to optimize presentation and absorption of ingested nutrients and/or pharmacologically active agents in the small intestine to prevent and/or reduce ineffectiveness thereof due to malabsorption.

The present invention further provides methods and compositions for enhancing the bioavailability and therapeutic effectiveness of pharmacologically active agents.

63 Claims, No Drawings

OTHER PUBLICATIONS

Hayashi, et al., "Fat feeding increases size, but not number, of chylomicrons produced by small intestine," *Am. J. Clin. Nutr.,* 20:816–824 (1967).

Huge, A., et al., "Effects of Enteral Feedback Inhibition on Motility, Luminal Flow, and Absorption of Nutrients in Proximal Gut of Minipigs," *Dig. Dis Sci.,* 40(5):1024–1034 (May 1995).

Irwin and Feeley, "Frequency and Size of Meals and Serum Lipids, Nitrogen and Mineral Retention, Fat Digestibility, and Ur inary Thiamine and Riboflavin in Young Women," *Am. J. Clin. Nutr.,* 20:816–824 (1967).

Jagannathan, et al., "Effects of Gormandizing and Semicontinuous Eating of Equicaloric Amounts of Formula–type High Fat Diets on Plasma Cholesterol and Triglyceride Levels in Human Volunteer Subjects," *Am. Clin. Nutr.,* 15:90–93 (1964).

Jenkins, et al., "Nibbling Versus Gorging: Metabolic Advantages of Increased Meal Frequency," *N. Eng. J. Med.,* 2:388–391 (1978).

Jenkins, et al., "Severity of coronary atherosclerosis related to lipoprotein concentration," *Br. Med. J.,* 2:388–391 (1978).

Keinke, et al., "Mechanical Factors Regulating Gastric Emptying of Viscous Nutrient Meals in Dogs," *Q. J. Exp. Physiol.,* 69:781–795 (1984).

Keinke and Ehrlein, "Effect of Oleic Acid on Canine Gastroduodenal Motility, Pyloric Diameter and Gastric Emptying," *Q. J. Exp. Physiol.,* 68:675–686 (1983).

Khoslas and Davis, "The effect of polycarbophil on the gastric emptying of pellets," *J. Pharm. Pharmacol.,* 39:47–49 (1987).

Lin, et al., "Acute Desensitization of Intestinal Motility Response," (abstract) *Gastroenterology,* 103:1392 (1992).

Lin, et al., "Inhibition of gastric emptying by glucose depends on the length of the intestine exposed to the nutrient," *Am. J. Physiol.,* 256:G404–G411 (1989).

Lin, et al., "Inhibition of gastric emptying by sodium oleate depends on the length of intestine exposed to the nutrients," *Am. J. Physiol.,* 259:G1031–G1036 (1990).

Lin, H.C., "Inhibition of Intestinal Transit by Fat Depends on Length of Exposure to Nutrient," *Gastroenterology,* 106:A531 (Apr. 1994).

Lin, H.C., et al., "Jejunal Brake Inhibition of Intestinal Transit by Fat in the Proximal Small Intestine," *Dig. Dis. Sci.,* 41(2):326–329 (Feb. 1996).

Lin, H.C., "Oleate Slows Upper Gut Transit and Reduces Diarrhea in Patients with Rapid Upper Gut Transit and Diarrhea," *Gastroenterology,* 108(4):A638 (1995).

Maida and Howlett, "Effects of cigarette smoking and dietary lipids on rat lipoprotein metabolism," *Atherosclerosis,* 80:209–216 (1990).

McGill, H.C., "Potential Mechanisms for the Augmentation of Atherosclerosis and Atherosclerotic Disese by Cigarette Smoking," *Preventive Medicine,* 8:390–403 (1979).

Mjos, et al., "Characterization of Remnants Produced During the Metabolism of TrigylcerideRich Lipoproteins of Blood Plasma and Intestinal Lymph in the Rat," *J. Clin. Inv.,* 56:603–615 (1975).

Ohtani, N., et al., "Mediators For Ileal Brake Differ Between the Stomach and Small Intestine in Conscious Dogs," *Gastroenterology,* 108(4 Supp.) abst. 660 (1995).

Pironi, L., et al. "Fat–Induced Ileal Brake in Humans: A Dose–Dependent Phenomenon Correlated to the Plasma Levels of Peptide YY," *Gastroenterology,* 105(3):733–739 (Sep. 1993).

Read, et al., "Effect of Infusion of Nutrient Solutions Into the Ileum on Gastrointestinal Transit and Plasma Levels of Neurotensin and Enteroglucagon," *Gastroenterology,* 86(2):274–280 (1984).

Redgrave and Carlson, "Changes in plasma very low density and low density lipoprotein content, composition and size after a fatty meal in normo–and hypertriglyceridemic man," *J. Lipid Res.,* 20:217–229 (1979).

Saunders, D.R., et al. "Absorption of triglyceride by human small intestine: dose–response relationships," *Am. Jour. Clin. Nutr.,* 48(4):988–991 (Oct. 1988).

Schemann and Ehrlein, "Postprandial Patterns of Canine Jejunal Motility and Transit of Luminal Content," *Gastroenterology,* 90:991–1000 (1986).

Schemann and Ehrlein, "The Utility of Oellulose Meals for Studies on Gastrointestinal Motility in Dogs," *Digestion* 25:194–196 (1982).

Siegle, M.L., et al., "Effects of ileal infusions of nutrients on motor patterns of canine small intestine," *Am. Jour. Physiol.,* 259(1 pt 1):G78–G85 (Jul. 1990).

Soper, N.J., et al., "The 'Ileal Brake' After Ileal Pouch–Anal Anastomosis," *Gastroenterology,* 98(1):111–116 (Jan. 1990).

Spiller, et al., "Further characterization of the "ileal brake" reflex in man—effect of ileal infusion of partial digests of fat, protein, and starch on jejunal motility and release of neurotensin, enteroglucagon, and peptide YY," *Gut,* 29:1042–1051 (1988).

Spiller, R.C., et al., "The ileal brake—inhibition of jejunal motility after ileal fat perfusion in man," *Gut,* 25(4):326–329 (1984).

Summers, et al., "Computerized Analysis of Spike Burst Activity in the Small intestine," *IEEE Trans. Bio. Eng.,* 29(5):309–314 (1982).

Swinyard and Lowenthal, "Pharmaceutical Necessities," *Remington's Pharmaceutical Sciences,* 17th Ed., AR Gennaro Ed. p. 1296 (1985).

Warnick, G.R., "Enzymatic Methods for Quantification of Lipoprotein Lipids," *Methods in Enzymology,* 129:101–123 (1986).

Welch. et al., "Effect of ileal infusion of lipid on jejunal motor patterns after a nutrient and nonnutrient meal," *Am. J. Physiol.,* 255:G800–G806 (1988).

Wu and Clark, "Resistance of intestinal triglyceride transport capapcity in the rat to adaptation to altered luminal environment," *Am. J. Clin. Nutr.,* 29:157–168 (1976).

Wu, et al., Composition of lymph chylomicrons from proximal or distal rat small intestine, *Am. J. Clin. Nutr.,* 33:582–589 (1980).

Wu, et al., "Transmucosal triglyceride transport rates in proximal an distal intestine in vivo," *J. Lipid Res.,* 16:251–257 (1975).

Zhou, X.T., et al., "Fat in Distal Gut Inhibits Intestinal Transit More Potently Than Fat in Proximal Gut," *Gastroenterology,* 108(4):A714 (Apr. 1995).

Zilversmit, DB., "Atherogenesis: A postprandial phenomenon," *Circulation,* 60(3):473–485 (1979).

Zilversmit, D.B., "Chylomicrons," Chapter in *Structural and Functional Aspects of Lipoproteins in Living Systems* Tria and Scanu Eds. Academic (press) New York, NY, pp. 329–368 (1969).

METHODS AND COMPOSITIONS FOR IMPROVING DIGESTION AND ABSORPTION IN THE SMALL INTESTINE

This application is a continuation of application Ser. No. 08/442,843 filed May 17, 1995 which application is now abandoned.

FIELD OF THE INVENTION

The present invention relates to methods and pharmaceutical compositions for controlling the presentation of luminal content in the gastrointestinal tract.

BACKGROUND OF THE INVENTION

A principal function of the gastrointestinal tract is to process and absorb food. The stomach, which is both a storage and digestive organ, works to optimize the conditions for the digestion and absorption of food in the small intestine. Following the stomach and preceding the large bowel (colon) is the small intestine which comprises three regions: the duodenum, jejunum, and ileum. A major function of the small intestine is one of absorption of digested nutrients.

The passage of a meal through the, gastrointestinal tract, which leads to digestion and absorption of nutrients, is controlled by a complex system of inhibitory and stimulatory motility mechanisms which are set in motion by the composition of the meal ingested. Specific receptors for fats, and proteins, and the osmolality, acidity and particle size of the meal activate propulsive and inhibitory reactions, which modulate transit and thus absorption. The rate of passage through the small intestine is of great significance for the rate and extent of absorption from the small intestine.

Disruption of the normal digestive and absorptive processes frequently manifests as a variety of syndromes, such as, for example malnutrition, weight loss, diarrhea, steatorrhea, vitamin deficiency, electrolyte imbalance, and the like.

The small intestine is also an important site for the absorption of pharmacological agents. The proximal part of the small intestine has the greatest capacity for absorption of drugs. Intestinal absorption of drugs is influenced to a great extent by many of the same basic factors that affect the digestion and absorption of nutrients, water and electrolytes.

Absorption of a drug in the gastrointestinal tract is a function of characteristics of the drug, such as its molecular structure, as well as attributes of the gastrointestinal tract. The rate of absorption of certain drugs, which are absorbed slowly and usually incompletely, varies according to the small intestine transit time. Intestinal transit is important in the design of pharmaceutical preparations, especially when the absorption site of a drug is located in a particular segment of the gastrointestinal tract.

Many drugs and dosage formulations have been and continue to be developed because of the need to overcome the physiological and physicochemical limitations associated with drug delivery such as poor stability, short biological half-life, inefficient absorption and poor bioavailability. Applications of controlled release technology have moved towards control of absorption via regulation of the input to the gastrointestinal tract. However, recent pharmaceutical attempts to alter gastric emptying and small intestinal transit times have not been very successful. (Khosla and Davis, *J. Pharm. Pharmacol.* 39:47–49 (1987); Davis et al., *Pharm. Res.* 3:208–213 (1986)).

For drug absorption to proceed efficiently, the drug must first arrive at a normal absorbing surface in a form suitable for absorption; it must remain there long enough in a form and in a concentration that enhance absorption; and it must be absorbed by a normal epithelial cell without being metabolized by that cell. Accordingly, considerable advantage would be obtained if a pharmaceutical dosage form could be retained for a longer period of time within the stomach and/or the small intestine for proper absorption to occur.

The period of time during which nutrients and/or drugs are in contact with the mucosa of the small intestine is crucial for the efficacy of digestion and absorption. Therefore, modulation of the motility rate and transit time of nutrients and/or pharmacologically active agents through the gastrointestinal tract will ensure optimal utilization of the absorptive surface, as well as prevent transport mechanisms from being overloaded (which could occur if substrates were passed on too rapidly and exceeded the absorptive capacity of already maximally loaded surfaces in the small intestine).

Thus, a need exists for optimizing absorption of ingested nutrients and/or pharmacologically active agents in the small intestine to prevent and/or reduce ineffectiveness thereof due to malabsorption. A need also exists for means to enhance the bioavailability and effectiveness of pharmacologically active agents. The present invention satisfies these needs and provides related advantages as well.

SUMMARY OF THE INVENTION

The present invention provides methods and compositions for slowing gastrointestinal transit and prolonging residence time to optimize presentation and absorption of ingested nutrients and/or pharmacologically active agents in the small intestine to prevent and/or reduce ineffectiveness thereof due to malabsorption.

The present invention further provides methods and compositions for enhancing the bioavailability and therapeutic effectiveness of pharmacologically active agents.

DETAILED DESCRIPTION OF THE INVENTION

Important steps in dietary lipid absorption begin in the stomach, where an intricate control system of inhibitory and stimulatory motility mechanisms are set in motion by the composition of the meal ingested. These mechanisms prevent too rapid emptying of gastric contents into the duodenum, which would overwhelm its capacity for lipid or fat absorption. Such preventative mechanisms ensure a maximum interface of the water-insoluble lipid with the aqueous contents of the intestinal tract.

The next step in absorption of fats or lipids occurs upon their entry into the small intestine. In the early portion of the small intestine, specific receptors for fats, and proteins, and the osmolality, acidity and the particle size of the meal activate propulsive and inhibitory reactions (i.e., ileal braking), which modulate their transit and absorption. The rate of passage through the small intestine (i.e., intestinal transit time) is of great significance for the rate and extent of absorption from the small intestine.

In the duodenum, the fats which have been released from the stomach encounter bile acids and pancreatic enzymes. The function of the bile acids is to render soluble the insoluble triglyceride molecules.

The intestinal absorption of lipids is normally very efficient over wide ranges of dietary fat intake. A normal person generally absorbs approximately 95–98% of dietary lipid. When the normal digestive and absorptive processes are impaired, malabsorption syndromes frequently ensue.

Malabsorption syndromes include a large heterogeneous group of gastrointestinal disorders with the common characteristic of failure to assimilate ingested substances normally. The defect is characterized by decreased or impaired function of almost any organ of the gut, including the liver, biliary tract, pancreas, and lymphatic system, as well as the intestine. The clinical manifestations may vary from a severe symptom complex of rapid intestinal transit, dumping syndrome, diarrhea, weight loss, distention, steatorrhea, and asthenia to symptoms of specific nutrient deficiencies (i.e., malnutrition).

Examples of gastrointestinal disorders that frequently manifest as one or more malabsorption syndromes are postgastrectomy syndrome, dumping syndrome, AIDS-associated chronic diarrhea, diabetes-associated diarrhea, postvagotomy diarrhea, bariatric surgery-associated diarrhea (including obesity surgeries: gastric bypass, gastroplasties and intestinal bypass), short bowel syndrome (including resection of the small intestine after trauma, radiation induced complications, Crohn's disease, infarction of the intestine from vascular occlusion), tube-feeding related diarrhea, chronic secretory diarrhea, carcinoid syndrome-associated diarrhea, gastrointestinal peptide tumors, endocrine tumors, chronic diarrhea associated with thyroid disorders, chronic diarrhea in bacterial overgrowth, chronic diarrhea in gastrinoma, choleraic diarrhea, chronic diarrhea in giardiasis, antibiotic-associated chronic diarrhea, diarrhea-predominant irritable bowel syndrome, chronic diarrhea associated with maldigestion and malabsorption, chronic diarrhea in idiopathis primary gastrointestinal motility disorders, chronic diarrhea associated with collagenous colitis, surgery-associated acute diarrhea, antibiotic-associated acute diarrhea, infection-associated acute infectious diarrhea, and the like.

The rate at which food passes through the gastrointestinal tract is an important factor that affects the absorptive capacity and the outcome following gastric surgery and/or intestinal resection. Resection of extensive sections of bowel as well as loss of absorptive surface secondary to diseased small bowel mucosa can lead to specific malabsorption syndromes. Resection or disease of large amounts of terminal ileum are known to cause vitamin B12 and bile acid deficiencies, which, in turn, can lead to fat and other fat-soluble substances being less well absorbed. Bypassed loops of bowel, created by either surgery or fistula formation, and strictures can result in blind loop syndromes with bacterial overgrowth and subsequent malabsorption.

Malnutrition is a common problem in patients with inflammatory bowel diseases such as, for example, Crohn's disease or ulcerative colitis. Weight loss is found in 70–80% of patients with Crohn's disease and 18–62% of patients with ulcerative colitis.

The role of nutritional support as a primary therapy for inflammatory bowel diseases is not well established. Given the natural history of inflammatory bowel diseases, with frequent relapses and spontaneous remissions, and the difficulty and variability in quantifying disease activity, it has been difficult to design clinical trials that definitively establish the role of nutrition as a primary therapy for inflammatory bowel diseases. The use of elemental diets as primary therapy for inflammatory bowel diseases has also been examined. Parenteral nutrition and elemental diets appear to have limited roles in the long-term treatment of patients with inflammatory bowel diseases.

Short bowel syndrome generally refers to a condition in which less than 150 cm of remaining small bowel is associated with a massive loss of absorptive capacity. It is characterized by severe diarrhea and malabsorption. Patients with short bowel syndrome often experience malabsorption of protein, carbohydrate and fat resulting in calorie depletion and steatorrhea.

The most important therapeutic objective in the management of short bowel is to maintain the patient's nutritional status. By necessity, it is achieved primarily by parenteral nutrition support in the early postoperative period. Enteral nutrition support can be started early after operation when the ileus has resolved. Maximization of enteral absorption of nutrients is important for long-term survival. Generally, such maximization requires that the enteral intake greatly exceed the absorptive needs to ensure that the nutritional requirements are met.

Functional pancreatic insufficiency may also cause steatorrhea after gastric resection. Steatorrhea is the presence of excess fat in the feces. It is usually caused by a defect in gastrointestinal digestion and/or absorption. Steatorrhea rarely exists without malabsorption of other substances. For example, conditions such as osteomalacia related to calcium and vitamin D deficiency or anemia due to selective iron or B12 deficiencies are often associated with the malabsorption that occurs with steatorrhea. Weight loss occurs because of a loss of nutrients and energy. Diarrhea is another major symptom associated with steatorrhea. It is present in 80–97% of patients with malabsorption.

Dumping syndrome is one of the most common causes of morbidity after gastric surgery. This syndrome is characterized by both gastrointestinal and vasomotor symptoms. Gastrointestinal symptoms include postprandial fullness, crampy abdominal pain, nausea, vomiting and explosive diarrhea. Vasomotor symptoms include, diaphoresis, weakness, dizziness, flushing, palpitations, and an intense desire to lie down. Patients with severe dumping symptoms may limit their food intake to minimize symptoms and as a result lose weight and become malnourished. In severe cases, as a last resort surgical treatment of dumping syndrome has been utilized.

Pharmaceutical treatment for severe dumping includes octreotide acetate (Sandoz), a long acting somatostatin analogue, which has been used with some success. Octreotide is administered subcutaneously and acts to slow gastric emptying, inhibit insulin release, and decrease enteric peptide secretion. Octreotide, unfortunately, is accompanied by several complications, which include injection site pain, tachyphylaxis, iatrogenic diabetes, malabsorption and cholelithiasis.

Diarrhea is a common problem after any abdominal operation. Treatment includes simple dietary changes, opiates and/or opiod-type drugs such as Lomotil or paregoric, antidiarrheal agents such as Diasorb (attapulgite), Donnagel (kaolin, hydroscyamine sulfate, atropine,sulfate and scopalamine hydrobromide), Kaopectate, Motofen (difenoxin hydrochloride and atropine sulfate) and Pepto-Bismol for inhibitory effect on intestinal transit.

Each modality of treatment, however, has had limited success and with the exception of dietary changes, all have negative side effects associated with use.

Diarrhea is also a common complication associated with enteral feeding. Multiple etiologies for diarrhea are postulated, and its genesis may be a multifactorial process (Edes et al., *Am. J. Med.* 88:91–93 (1990)). Causes include concurrent use of antibiotics or other diarrhea-inducing medications, altered bacterial flora, formula composition, rate of infusion, hypoalbuminemia, and enteral formula contamination. The composition of formula may also affect the incidence of diarrhea. The use of fiber-containing formulas to control diarrhea related to tube feeding is unsettled (Frankenfield et al., *Am. J. Clin. Nutr.* 50:553–58 (1989)).

A tremendous amount of research has been undertaken in attempting to elucidate the role of nutrition and absorption in gastrointestinal disorders. Despite this research, few standards of care presently exist for the use of nutrition and absorption in most aspects of these disorders.

Accordingly, the present invention provides methods of slowing gastrointestinal transit to prolong the residence time of a substance in the small intestine of a subject for an amount of time sufficient for digestion and absorption of the substance to occur therein. Invention methods comprise administering to a subject a composition comprising an active lipid in an amount effective to slow the transit of said substance through the small intestine for an amount of time sufficient for absorption of said substance to occur therein.

The invention contemplates a range of optimal residence times which are dependent upon the character of the substance (i.e., nutrients, pharmacologically active agents). As used herein, "substance" encompasses the luminal content of the gastrointestinal tract which includes, for example, digested and partially digested foods and nutrients, dissolved and/or solubilized pharmacologically active agents as well as incompletely dissolved and/or solubilized forms thereof, electrolyte-containing luminal fluids, and the like.

The small intestinal residence time for optimal absorption of digested foods and nutrients can be calculated using an average orocecal transit time as a reference. The normal orocecal transit time is approximately 2–3 hours in the fasted state. The invention composition should target an intestinal residence within the same average time frame of approximately 2–3 hours.

The pharmaceutical industry has published a great deal of information on the dissolution time for individual pharmacologically active agents and compounds. Such information is found in the numerous pharmacological publications which are readily available to those of skill in the art. For example, if the in vitro model for dissolution and release of agent "X" is 4 hours, then the small intestinal residence time for optimal absorption of agent "X" would be at least 4 hours and would also include additional time allowing for gastric emptying to occur in vivo. Thus, for pharmacologically active agents, the appropriate residence time is dependent on the time for release of the active agent.

As used herein, "digestion" encompasses the process of breaking down large molecules into their smaller component molecules.

As used herein, "absorption" encompasses the transport of a substance from the intestinal lumen through the barrier of the mucosal epithelial cells into the blood and/or lymphatic systems.

Invention compositions comprise an active lipid and a pharmaceutically acceptable carrier. A major function of invention compositions is to slow gastrointestinal transit and control gastrointestinal intestinal residence time of a substance to enable substantial completion of luminal and mucosal events required for absorption of the substance to occur in the small intestine. Of equal significance is the function of invention compositions to control the presentation of a substance to a desired region of the small intestine for absorption.

In a preferred embodiment, invention compositions limit the presentation of a substance to the proximal region of the small intestine for absorption.

As used herein, "active lipid" encompasses a digested or substantially digested molecule having a structure and function substantially similar to a hydrolyzed end-product of fat digestion. Examples of hydrolyzed end products are molecules such as glycerol and fatty acids.

In a preferred embodiment, the active lipid comprises a saturated or unsaturated fatty acid. Fatty acids contemplated by the invention include fatty acids having between 4 and 24 carbon atoms.

Examples of fatty acids contemplated for use in the practice of the present invention include caprolic acid, caprulic acid, capric acid, lauric acid, myristic acid, oleic acid, palmitic acid, stearic acid, palmitoleic acid, linoleic acid, linolenic acid, trans-hexadecanoic acid, elaidic acid, columbinic acid, arachidic acid, behenic acid eicosenoic acid, erucic acid, bressidic acid, cetoleic acid, nervonic acid, Mead acid, arachidonic acid, timnodonic acid, clupanodonic acid, docosahexaenoic acid, and the like. In a preferred embodiment, the active lipid comprises oleic acid.

The active lipids suitable for use with this invention are employed in well dispersed form in a pharmaceutically acceptable carrier. As used herein, "pharmaceutically acceptable carrier" encompasses any of the standard pharmaceutical carriers known to those of skill in the art. Dispersion can be accomplished in various ways. The first is that of a solution. Lipids can be held in solution if the solution has the properties of bile (i.e., solution of mixed micelles with bile salt added), or the solution has the properties of a detergent (e.g., pH 9.6 carbonate buffer) or a solvent (e.g., solution of Tween). The second is an emulsion which is a 2-phase system in which one liquid is dispersed in the form of small globules throughout another liquid that is immiscible with the first liquid (Swinyard and Lowenthal, "Pharmaceutical Necessities" *REMINGTON'S PHARMACEUTICAL SCIENCES*, 17th ed., AR Gennaro (Ed), Philadelphia College of Pharmacy and Science, 1985 p.1296). The third is a suspension with dispersed solids (e.g., microcrystalline suspension). Additionally, any emulsifying and suspending agent that is acceptable for human consumption can be used as a vehicle for dispersion of the composition. For example, gum acacia, agar, sodium alginate, bentonite, carbomer, carboxymethylcellulose, carrageenan, powdered cellulose, cholesterol, gelatin, hydroxyethyl cellulose, hydroxypropyl cellulose, hydroxypropyl methylcellulose, methylcellulose, octoxynol 9, oleyl alcohol, polyvinyl alcohol, povidone, propylene glycol monostearate, sodium lauryl sulfate, sorbitan esters, stearyl alcohol, tragacanth, xantham gum, chondrus, glycerin, trolamine, coconut oil, propylene glycol, thyl alcoholmalt and malt extract. Any of these solutions, emulsions or suspensions can be incorporated into capsules, or a microsphere or particle (coated or not) contained in a capsule.

The compositions of the invention containing the active lipid may be in a form suitable for oral or enteral use, for example, as tablets, troches, lozenges, aqueous or oily suspensions, dispersible powders or granules, emulsions, hard or soft capsules, syrups, elixirs or enteral formulas. Compositions intended for oral use may be prepared according to any method known to the art for the manufacture of pharmaceutical compositions. Compositions may also be coated by the techniques described in the U.S. Pat. Nos. 4,256,108; 4,160,452; and 4,265,874, to form osmotic therapeutic tablets for controlled release. Other techniques for controlled release compositions, such as those described in the U.S. Pat. Nos. 4,193,985; and 4,690,822; 4,572,833 may be used in the formulation of invention compositions.

An effective amount of active lipid is any amount that is effective to slow gastrointestinal transit and control presentation of a substance to a desired region of the small intestine. For example, an effective amount of active lipid, as contemplated by the instant invention, is any amount of active lipid that can trigger any or all of the following reflexes: intestino-lower esophageal sphincter (relaxation of LES); intestino-gastric feedback (inhibition of gastric emptying); intestino-intestinal feedback (ileo-jejunal feedback/ileal brake, jejuno-jejunal feedback/jejunal brake, intestino-CNS feedback (for example, intensifying intestinal signalling of satiety)); intestino-pancreatic feedback (control of exocrine enzyme output); intestino-biliary feedback (control of bile flow); intestino-mesenteric blood flow feedback (for the control of mucosal hyperemia); intestino-colonic feedback (so called gastro-colonic reflex whereby the colon contracts in response to nutrients in the proximal small intestine).

Methods of administration are well known to those of skill in the art and include, but are not limited to oral administration, parenteral administration and enteral administration. In a preferred embodiment, the composition of the invention is administered in a load-dependent manner which ensures that the dispersion of active lipid is presented to the entire length of the small intestine. Administration will be in a dosage such that the desired effect is produced. In a preferred embodiment, the load of active lipid is from about 0.5 grams to about 2.0 grams.

In order to stretch biologic activity so that one has a convenient, daily dosage regimen, the present invention contemplates that invention compositions are administered prior to ingestion of the food, nutrient and/or pharmacologically active agent. In a preferred embodiment, invention compositions (depending on the formulation) are administered up to a period of 24 hours prior to ingestion of the food, nutrient and/or pharmacologically active agent. The period of time prior to ingestion is determined on the precise formulation of the composition. For example, if the formulation incorporates a controlled release system, the duration of release and activation of the active lipid will determine the time for administration of the composition. Sustained release formulation of the composition is useful to ensure that the feedback effect is sustained.

The use of invention compositions in enteral feeding contemplates adding the composition directly to the feeding formula. Invention compositions can either be compounded as needed into the enteral formula when the rate of formula delivery is known (i.e., add just enough composition to deliver the load of active lipids). Alternatively, the composition of the invention may be compounded at the factory so that the enteral formulas are produced having different concentrations of the composition and may be used according to the rate of formula delivery (i.e., higher concentration of composition for lower rate of delivery).

If the invention composition were to be added to an enteral formula and the formula is continuously delivered into the small intestine, the composition that is initially presented with the nutrient formula would be slowing the transit of nutrients that are delivered later.

Except for the start of feeding when transit may be too rapid because the inhibitory feedback from the composition has yet to be fully activated, once equilibrium is established, it is no longer logistically an issue of delivering the composition as a premeal although the physiologic principle is still the same.

Before dietary fats can be absorbed, the motor activities of the small intestine in the postprandial period must first move the output from the stomach to the appropriate absorptive sites of the small intestine. To achieve the goal of optimizing the movement of a substance through the small intestine, the temporal and spatial patterns of intestinal motility are specifically controlled by the nutrients of the luminal content.

Without wishing to be bound by any theory, it is presently believed that early in gastric emptying, before inhibitory feedback is activated, the load of fat entering the small intestine may be variable and dependent on the load of fat in the meal. Thus, while exposure to fat may be limited to the proximal small bowel after a small load, a larger load, by overwhelming more proximal absorptive sites, may spill further along the small bowel to expose the distal small bowel to fat. Thus, the response of the duodenum to fat limits the spread of fat so that more absorption can be completed in the proximal small intestine and less in the distal small intestine. Furthermore, since the speed of movement of luminal fat must decrease when more fat enters the duodenum, in order to avoid steatorrhea, intestinal transit is inhibited in a load-dependent fashion by fat. This precise regulation of intestinal transit occurs whether the region of exposure to fat is confined to the proximal gut or extended to the distal gut.

In accordance with the present invention it has been observed that inhibition of intestinal transit by fat depends on the load of fat entering the small intestine. More specifically, that intestinal transit is inhibited by fat in a load-dependent fashion whether the nutrient is confined to the proximal segment of the small bowel or allowed access to the whole gut.

Accordingly, the present invention provides a method of slowing gastrointestinal transit in a subject having a gastrointestinal disorder, said method comprising administering to said subject a composition comprising an active lipid in an amount sufficient to prolong the residence time of a substance in the small intestine.

Invention methods and compositions are useful in the management of nutritional and absorption in subjects having a variety of gastrointestinal symptoms such as, rapid intestinal transit, dumping syndrome, diarrhea, weight loss, distention, steatorrhea, and asthenia to symptoms of specific nutrient deficiencies (i.e., malnutrition).

Examples of gastrointestinal disorders that invention methods and compositions are therapeutic include postgastrectomy syndrome, dumping syndrome, AIDS-associated chronic diarrhea, diabetes-associated diarrhea, postvagotomy diarrhea, bariatric surgery-associated diarrhea (including obesity surgeries: gastric bypass, gastroplasties and intestinal bypass), short bowel syndrome (including resection of the small intestine after trauma, radiation induced complications, Crohn's disease, infarction of the intestine from vascular occlusion), tube-feeding related diarrhea, chronic secretory diarrhea, carcinoid syndrome-associated diarrhea, gastrointestinal peptide tumors, endocrine tumors, chronic diarrhea associated with thyroid disorders, chronic diarrhea in bacterial overgrowth, chronic diarrhea in gastrinoma, choleraic diarrhea, chronic diarrhea in giardiasis, antibiotic-associated chronic diarrhea, diarrhea-predominant irritable bowel syndrome, chronic diarrhea associated with maldigestion and malabsorption, chronic diarrhea in idiopathis primary gastrointestinal motility disorders, chronic diarrhea associated with collagenous colitis, surgery-associated acute diarrhea, antibiotic-associated acute diarrhea, infection-associated acute infectious diarrhea, and the like.

The instant invention further provides a method and composition for treating diarrhea in a subject, said method comprising administering to said subject a composition comprising an active lipid in an amount sufficient to prolong the residence time of the luminal contents of the small intestine. The invention composition can be delivered as a single unit, multiple unit (for more prolonged effect via enterically coated or sustained release forms) or in a liquid form.

Since cholesterol and triglycerides are so insoluble in plasma, after mucosal absorption of lipids, the transport of these lipids from the intestine to the liver occurs through lipoproteins called chylomicrons.

While fat absorption from the lumen is rate-limiting for the proximal half of the small intestine, chylomicron synthesis or release is rate-limiting for the distal one half of the small intestine. As a result, chylomicrons formed by the distal small intestine are larger than those from the proximal small intestine (Wu, 1975). In the capillary bed of the peripheral circulatory system, the enzyme lipoprotein lipase hydrolyzes and removes most of the triglycerides from the chylomicron. The lipoprotein that remains, now rich in cholesterol esters and potentially atherogenic, is called a chylomicron remnant. This postprandial lipoprotein is then removed from the circulation by the liver (Zilversmit, Circulation 60(3):473 (1979)).

Elevated levels of atherogenic serum lipids have been directly correlated with atherosclerosis (Keinke et al., Q. J. Exp. Physiol. 69:781–795 (1984)).

The present invention provides a novel method to minimize atherogenic postprandial lipemia by optimizing proximal fat absorption. In other words, the present invention provides a novel method by which atherogenic serum lipids can be controlled preabsorptively by the fed motility response of the small intestine to luminal fat.

Preabsorptive control depends on the triggering of a specific pattern of proximal intestinal motility which slows transit to minimize the spread of fat into the distal gut. After a small meal of cholesterol-containing, fatty foods, the small intestine limits the site of fat absorption to the proximal small intestine by generating nonpropagated motility to slow intestinal transit. Since chylomicrons produced by the proximal small intestine are small in size, the size distribution of postprandial lipoproteins is shifted to minimize postprandial lipemia. However, during gorging of a high cholesterol, high fat meal, the ability of the small intestine to optimize proximal fat absorption is reduced by the time-dependent fading of the effect of fat on nonpropagated motility. As a result, after the first 1–2 hours, faster intestinal transit works to displace luminal fat into the distal small intestine where large, cholesterol-enriched, atherogenic chylomicrons are formed and released into the circulation.

In addition to the dietary effects on intestinal transit, studies suggest that nicotine inhibits intestinal motility. (McGill, 1979, Maida, 1990) (Booyse, 1981) (Carlson 1970). In the postprandial situation, this nicotine-related inhibitory effect alters the potentially protective, braking or nonpropagated pattern of motility. As a result, nicotine may facilitate the spreading of ingested lipids into the distal small intestine and impair the preabsorptive control of lipids. The methods of the present invention provide means to minimize the nicotine-induced inhibition of this postprandial response and to maximize proximal fat absorption.

Oral pharmaceutical preparations account for more than 80% of all drugs prescribed. It is essential, therefore, to control the multiple factors that influence their intestinal absorption as a determinant of ultimate therapeutic effectiveness.

Disintegration and dissolution are factors determining drug absorption that takes place only after a drug is in solution. Drugs ingested in solid form must first dissolve in the gastrointestinal fluid before they can be absorbed, and tablets must disintegrate before they can dissolve. The dissolution of a drug in the gastrointestinal tract is often the rate-limiting step governing its bioavailability. In any given drug, there can be a 2- to 5-fold difference in the rate or extent of gastrointestinal absorption, depending on the dosage or its formulation.

The rate of gastric emptying bears directly on the absorption of ingested drugs and on their bioavailability. Some drugs are metabolized or degraded in the stomach, and delayed gastric emptying reduces the amount of active drug available for absorption.

The pharmaceutical industry has developed all sorts of slow and/or sustained-release technology. These efforts have been directed to delaying gastric emptying. Sustained-release formulations employ several methods. The most common is a tablet containing an insoluble core; a drug applied to the outside layer is released soon after the medication is ingested, but drug trapped inside the core is released more slowly. Capsules containing multiparticulate units of drug with coatings that dissolve at different rates are designed to give a sustained-release effect. However, the basic problem with sustained-release medications is the considerable variability in their absorption due to the inability to monitor the individual's ingestion of the medication and thus, inability to control transit. Accordingly, slow release of drug in the absence of slow transit in the gut is meaningless.

The instant invention solves the bioavailability problem in this instance. The methods and compositions of this invention enable one to manipulate the balance of dissolution and gastrointestinal transit by increasing gastrointestinal residence time.

To facilitate drug absorption in the proximal small intestine, the present invention provides a method for prolonging the gastrointestinal residence time which will allow drugs in any dosage form to more completely dissolve and be absorbed. Since invention compositions slow gastrointestinal transit (delays both gastric emptying and small intestinal transit) a more rapid dissolving dosage form is preferred.

Accordingly, the present invention provides pharmaceutical oral articles and enteral formulas that slow gastrointestinal transit and prolong residence time of a substance. The composition of the invention enhance dissolution, absorption, and hence bioavailability of pharmacologically active agents ingested concurrently therewith or subsequent thereto.

Pharmaceutical compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable-carriers for tablets, pellets, capsules, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used.

The active lipid is included in the pharmaceutical composition in an amount sufficient to produce the desired effect upon the process or condition of diseases.

Pharmaceutical compositions containing the active lipid may be in a form suitable for oral use, for example, as tablets, troches, lozenges, aqueous or oily suspensions, dispersible powders or granules, emulsions, hard or soft capsules, syrups, elixirs or enteral formulas. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release. Other techniques for controlled release compositions, such as those described in the U.S. Pat. Nos. 4,193,985; and 4,690,822; 4,572,833 may be used in the formulation of invention pharmaceutical compositions.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

The methods and compositions of the invention are most needed for pharmacologically active agents that have slow dissolution characteristics. Since the active agent is released slowly such as formulations that are now enterically coated or packaged in a sustained release form, there is great potential for the drug to be passed into the colon still incompletely absorbed. The role of invention compositions is to increase the gastrointestinal residence time to allow the poorly dissoluting drugs to be fully absorbed.

In one embodiment of the present invention, the pharmaceutical article is an enterically coated or a sustained release form that intestinal transit is slowed for a prolonged period of time. The pharmacologically active agent can also be packaged in an enterically coated or sustained release form so that it can also be released slowly. This combination would probably have the longest biologic activity and be favored if a high initial drug plasma peak is not desirable.

In an alternative embodiment, invention pharmaceutical article may be formulated for controlled release (enterically coated or sustained release form) whereas a rapid release formulation is contemplated for the pharmacologically active agent (tablet or capsule with rapid dissolution characteristics or composition in a liquid form). This simpler strategy would be used if the claimed, composition is able to "hold" the active drug in the proximal small intestine for a period long enough for complete absorption of the drug to take place and a high initial peak of the drug is desirable.

Another embodiment of the instant invention contemplates a rapid release formulation of the composition/article. This form would be administered following slow release of the pharmacologically active agent which is enterically coated or a sustained release form.

Also contemplated by the instant invention is the combination of a rapid release form of the composition/article and a rapid release of the pharmacologically active agent.

Accordingly, the methods and compositions of the instant invention can be combined with the existing pharmaceutical release technology to provide control over not only the gastrointestinal transit and residence time of a pharmacologically active agent, but also over the time of release of the active agent. More specifically, the combination of invention methods and compositions with existing release technology provides control over the multiple factors that influence intestinal absorption of a pharmacologically active agent. The ability to control such factors enables optimization of the bioavailability and ultimate therapeutic effectiveness of any pharmacologically active agent.

The following examples are intended to illustrate, but not limit, the present invention.

EXAMPLE I

Oleate Slows Upper Gut Transit and Reduces Diarrhea in Patients with Rapid upper Gut Transit and Diarrhea Rapid transit through the upper gut may result in diarrhea, maldigestion and absorption, and weight loss; and pharmacologic treatment with opiates or anticholinergics often is required. It was tested whether fatty acids could be used to slow upper gut transit and reduce diarrhea in patients with rapid transit and diarrhea.

Five patients with persistent diarrhea for 3 to 22 months, (one each due to vagal denervation, ileal resection for Crohn's disease, and vagotomy and antrectomy, and two due to idiopathic causes) were studied. Each patient demonstrated rapid upper gut transit on routine lactulose breath hydrogen testing (or variations thereof measuring labelled carbon dioxide)(Cammack et al. *Gut* 23:957–961 (1982)). This test relies on the metabolism of certain carbohydrate materials (e.g. lactulose) by the microbial flora within the caecum. By generating gas which can be detected in the expired air, it is possible to make some estimation about the initial arrival of the administered material within the colon.

For the experimental study, each patient received orally in random order, 0, 1.6 or 3.2 ml of oleate in 25 ml Ensure (Ross), followed by 100 ml water. Thirty minutes after each dose of oleate, patients received 10 g lactulose orally, followed by 25 ml water. Breath hydrogen was measured every 10–15 minutes, and upper gut transit time was defined as the time from ingestion of lactulose until a rise of $H_2$ of >10 ppm. Data were analyzed using 1-way repeated measures analysis of variance (ANOVA).

| Results (mean ± SE): | | | |
|---|---|---|---|
| Oleate (ml) | 0 | 1.6 | 3.2 |
| Transit time (min) | 46 ± 8.6 | 116 ± 11.1 | 140 ± 11.5 |

Upper gut transit was significantly prolonged by oleate in a dose-dependent fashion (p<0.005, significant trend). During prolonged ingestion of oleate 15–30 minutes prior to meals, all patients reported reduced diarrhea. The patient with Crohn's disease reported complete resolution of chronic abdominal pain as well as post prandial bloating and nausea, and gained 22 lbs. In addition, the patient with vagotomy and antrectomy reported resolution of postprandial dumping syndrome (flushing, nausea, light-headedness).

These experiments demonstrate that oleate is effective to slow upper gut transit and reduce diarrhea among patients with rapid transit and diarrhea. It is likely that this novel treatment will be effective in other chronic diarrheal conditions associated with rapid transit.

EXAMPLE II

Fat in Distal Gut Inhibits Intestinal Transit More Potently Than Fat in Proximal Gut In 4 dogs equipped with duodenal (10 cm from pylorus) and midgut (160 cm from pylorus) fistulas, intestinal transit was compared across an isolated 150 cm test segment (between fistulas) while 0, 15, 30 or 60 mM oleate was delivered into either the proximal or distal segment of the gut as a solution of mixed micelles in pH 7.0 phosphate buffer at 2 ml/min for 90 minutes. The segment of gut not receiving oleate was perfused with buffer at 2 ml/min. 60 minutes after the start of the perfusion, ~20 $\mu$Ci of $^{99m}$Tc-DTPA (diethylenetriaminepentaacetic acid) was delivered as a bolus into the test segment. Intestinal transit was then measured by counting the radioactivity of 1 ml samples collected every 5 minutes from the diverted output of the midgut fistula.

Intestinal transit was calculated by determining the area under the curve (AUC) of the cumulative percent recovery of the radioactive marker. The square root values of the AUC (Sqrt AUC), where 0=no recovery by 30 minutes and 47.4=theoretical, instantaneous complete recovery by time 0, were compared across region of fat exposure and oleate dose using 2-way repeated measures ANOVA.

| | Oleate dose (mM) (mean ± SE) | | |
|---|---|---|---|
| Region of fat exposure | 15 | 30 | 60 |
| Proximal ½ of gut | 41.6 ± 1.4 | 40.6 ± 10.2 | 34.4 ± 3.0 |
| Distal ½ of gut | 25.6 ± 1.4 | 18.9 ± 1.5 | 7.0 ± 3.8 |

Control: buffer into both proximal and distal ½ of gut= 41.4±4.6.

These experiments demonstrate that intestinal transit is slower when fat is exposed in the distal ½ of gut (region effect p<0.01). These experiments also demonstrate that oleate is effective to inhibit intestinal transit in a dose-dependent fashion (dose effect, p<0.05); and that dose dependent inhibition of intestinal transit by oleate depends on the region of exposure (interaction between region and dose, p<0.01).

Although the invention has been described with reference to the disclosed embodiments, those skilled in the art will readily appreciate that the specific embodiments taught hereinabove are only illustrative of the invention. It should be understood that various modifications can be made without departing from the spirit of the invention.

What is claimed is:

1. A method for prolonging the residence time of an orally or enterally administered substance by promoting its dissolution, bioavailability and/or absorption in the small intestine, comprising administering to a subject in need of the treatment an anti-atherogenic, anti-diarrheal, digestion, dissolution and/or absorption promoting and/or gastrointestinal transit slowing composition comprising a carrier and a dispersion consisting essentially of an active lipid in the carriers, the active lipid being selected from the group consisting of saturated and unsaturated fatty acids, fully hydrolyzed fats and mixtures thereof, in an amount and a form effective to promote contact of the lipid with the subject's small intestine and, thereby, prolong the residence time of an orally or enterally administered substance dissolution, bioavailability and/or through the small intestine for a period of time effective to increase substance absorption there through.

2. The method of claim 1, wherein the anti-atherogenic, anti-diarrheal, digestion, dissolution and/or absorption promoting and/or gastrointestinal transit slowing composition is administered orally.

3. The method of claim 2, wherein the anti-atherogenic, anti-diarrheal, digestion, dissolution and/or absorption promoting and/or gastrointestinal transit slowing composition is administered up to about 24 hours prior to the administration of the substance.

4. The method of claim 1, wherein the anti-atherogenic, anti-diarrheal, digestion, dissolution and/or absorption promoting and/or gastrointestinal transit slowing composition is administered concurrently with the substance.

5. The method of claim 1, wherein the anti-atherogenic, anti-diarrheal, digestion, dissolution and/or absorption promoting and/or gastrointestinal transit slowing composition is a liquid or a solid.

6. The method of claim 1, wherein the anti-atherogenic, anti-diarrheal, digestion, dissolution and/or absorption promoting and/or gastrointestinal transit slowing composition is tube-delivered.

7. The method of claim 1, wherein the active lipid comprises fully hydrolyzed fats.

8. The method of claim 1, wherein the active lipid comprises a fatty acid.

9. The method of claim 8, wherein the fatty acid is selected from the group of ($C_4$–$C_{24}$) saturated and unsaturated fatty acids and mixtures thereof.

10. The method of claim 9, wherein the fatty acids are selected from the group consisting of caprolic acid, caprulic acid, capric acid, lauric acid, myristic acid, oleic acid, palmitic acid, stearic acid, palmitoleic acid, linoleic acid, linolenic acid, trans-hexadecanoic acid, elaidic acid, columbinic acid, arachidic acid, behenic acid eicosenoic acid, erucic acid, bressidic acid, cetoleic acid, nervonic acid, Mead acid, arachidonic acid, timnodonic acid, clupanodonic acid, docosahexaenoic acid and mixtures thereof.

11. The method of claim 10, wherein the fatty acid comprises oleic acid or mixtures thereof with other fatty acids.

12. A method of treating a gastrointestinal disorder by slowing the gastrointestinal transit of an orally or enterally administered substance in a subject, comprising administering to a subject in need of the treatment a composition comprising a carrier and a dispersion consisting essentially of an active lipid in the carrier, the active lipid being selected from the group consisting of saturated and unsaturated fatty acids, fully hydrolyzed fats and mixtures thereof, in an amount and in a form effective to promote contact of the lipid with the subject's small intestine and, thereby, slow the gastrointestinal transit of an orally or enterally administered substance through the small intestine.

13. The method of claim 12, wherein the gastrointestinal transit of the substance through the small intestine is slowed for a period of time effective for absorption of the substance to occur.

14. The method of claim 13, wherein the increased absorption of the substance is associated with the slowing of the gastrointestinal transit of the substance through the small intestine.

15. A method of enhancing the digestion and absorption of orally or enterally administered nutrients and/or pharmacological agents, comprising administering to a subject in need of the treatment a composition comprising a carrier and a dispersion consisting essentially of an active lipid in the carrier, the active lipid being selected from the group consisting of saturated and unsaturated fatty acids, fully hydrolyzed fats and mixtures thereof, in an amount and in a form effective to promote the contact of the active lipid with the small intestine and, thereby, prolong the residence time and enhance the digestion and absorption of orally or enterally administered nutrients and/or pharmacological agents in the small intestine.

16. A method for reducing diarrhea, comprising
administering to a subject in need of the treatment a composition comprising an active lipid selected from the group consisting of saturated and unsaturated fatty acids, fully hydrolyzed fats, and mixtures thereof, in an amount, and in a form effective to promote contact of the active lipid with the small intestine, and prolong the residence time of the luminal contents of the small intestine and, thereby, reduce diarrhea.

17. A method of reducing the serum level of atherogenic lipids derived from an ingested substance, comprising
administering to a subject in need of the treatment a composition comprising an active lipid selected from the group consisting of saturated and unsaturated fatty acids, fully hydrolyzed fats, and mixtures thereof, in an amount and in a form effective for promoting contact of the active lipid with small intestine, prolong the residence time in the small intestine of the ingested substance, and thereby, reduce atherogenic lipid serum levels.

18. The method of claim 17, wherein the composition is administered in an amount and in a form effective for limiting the spread and increasing the contact of the ingested substance with the proximal segment of the small intestine.

19. A method of enhancing the bioavailability of an orally ingested pharmacological agent by promoting a digestive, dissolving, absorptive, anti-atherogenic, anti-diarrheal and/ or gastrointestinal transit slowing effect, comprising administering to a subject in need of the treatment an anti-atherogenic, anti-diarrheal, digestion, dissolution and/or absorption promoting and/or gastrointestinal transit slowing composition comprising a carrier and a dispersion consisting essentially of an active lipid in the carrier, the active lipid being selected from the group consisting of saturated and unsaturated fatty acids, fully hydrolyzed lipid and mixtures thereof, in an amount and in a form effective for promoting the contact of the lipid with the subject's small intestine, promoting an anti-atherogenic, anti-diarrheal, digestive, dissolving and/or absorptive effect and, thereby, prolonging residence time, enhancing the dissolution, bioavailability and/or absorption of an ingested pharmacological agent in the small intestine.

20. The method of claim 19, wherein the anti-atherogenic, anti-diarrheal, digestion, dissolution and/or absorption promoting, and/or gastrointestinal transit slowing composition is administered prior to administration of the pharmacological agent.

21. The method of claim 20, wherein the anti-atherogenic, anti-diarrheal, digestion, dissolution and/or absorption promoting, and/or gastrointestinal transit slowing composition is administered about 5 to about 60 minutes prior to administration of the pharmacological agent.

22. The method of claim 19, wherein the anti-atherogenic, anti-diarrheal, digestion, dissolution and/or absorption promoting, and/or gastrointestinal transit slowing composition is administered concurrently with the agent.

23. An anti-atherogenic, anti-diarrheal, digestion, dissolution and/or absorption promoting and/or gastrointestinal transit slowing controlled release oral composition, comprising
a dispersion in a carrier of a plurality of particles which comprise an active lipid selected from the group consisting of saturated and unsaturated fatty acids, fully hydrolyzed fats and mixtures thereof; and
a controlled release coating thereon, which coating upon ingestion releases the active lipid and the particles and promotes their absorption, into the proximal segment of the small intestine by effecting and sustaining gastrointestinal transit slowing, dissolution, bioavailability and/or absorption promotion and/or an anti-diarrheal and/or anti-atherogenic effect.

24. An anti-atherogenic, anti-diarrheal, digestion, dissolution and/or absorption promoting and/or gastrointestinal transit slowing liquid enteral composition, comprising a liquid carrier and a dispersion in the carrier consisting essentially of a substance and an active lipid selected from the group consisting of saturated and unsaturated fatty acids, fully hydrolyzed fats, and mixtures thereof; which composition upon ingestion releases the active lipid into the proximal segment of the small intestine, so as to prolong the residence time of the substance in the small intestine and, thereby, increase substance digestion, dissolution, bioavailability and/or absorption and/or anti-diarrheal and/or anti-atherogenic effect.

25. A method of enhancing the absorption of a substance in the small intestine and promoting anti-atherogenes, anti-diarrheal, digestion, and/or dissolution, and/or slowing gastrointestinal transit, comprising
administering to a subject in need of the treatment the anti-atherogenic, anti-diarrheal, digestion, dissolution and/or absorption promoting, and/or gastrointestinal transit slowing liquid enteral composition of claim 24, in an amount and for a period of time effective for the active lipid to contact and be absorbed through the small intestine and, thereby, prolong the residence time, promote digestion, bioavailability and/or absorption of the substance in the small intestine and/or have an anti-diarrheal and/or anti-atherogenic effect.

26. A method of enhancing the absorption of an orally administered substance and promoting an anti-atherogenic and/or anti-diarrheal effect, and promoting digestion and dissolution, and slowing gastrointestinal transit, comprising administering to a subject in need of treatment an anti-atherogenic, anti-diarrheal, digestion, dissolution and/or absorption promoting and/or gastrointestinal transit slowing oral composition, comprising a core comprising a substance selected from the group consisting of nutrients and pharmacological agents and a coating thereon comprising an active lipid selected from the group consisting of saturated and unsaturated fatty acids and mixtures thereof, in an amount effective for promoting contact of the active lipid with, and its absorption from, the proximal segment of the small intestine, thereby prolonging the residence time and increasing the digestion and absorption of the substance in the small intestine and promoting an anti-atherogenic and/or anti-diarrheal effect.

27. An enteral anti-atherogenic, anti-diarrheal, digestion, dissolution and/or absorption promoting and/or gastrointestinal transit slowing composition, comprising
  a first component comprising an active ingredient to be absorbed through the small intestine;
  a second component comprising a carrier dispersible form of an active lipid selected from the group consisting of saturated and unsaturated fats, fully hydrolyzed fats and mixtures thereof; and
  an enteric coating which releases the first and the second components into the proximal segment of the small intestine, where the lipid slows transit and increases digestion, dissolution and/or residence time in, and absorption through, the small intestine without significant degradation and, thereby, increases absorption of the active ingredient thereof through in the presence of the active lipid than in its absence.

28. The anti-atherogenic, anti-diarrheal, digestion, dissolution and/or absorption promoting, and/or gastrointestinal transit slowing composition of claim 27, wherein the active ingredient is selected from the group consisting of nutrients and pharmacological agents.

29. The anti-atherogenic, anti-diarrheal, digestion, dissolution and/or absorption promoting and/or gastrointestinal transit slowing composition of claim 28, wherein the nutrients are selected from the group consisting of foodstuffs, vitamins and minerals.

30. The anti-atherogenic anti-diarrheal, digestion, dissolution and/or absorption promoting and/or gastrointestinal transit slowing composition of claim 28, wherein the pharmacological agents are selected from the group consisting of somatostatin analogues, insulin release inhibitors, anti-diarrheal agents, antibiotics, fiber and electrolytes.

31. The anti-atherogenic, anti-diarrheal, digestion, dissolution and/or absorption promoting, and/or gastrointestinal transit slowing composition of claim 27, further comprising an additional ingredient selected from the group consisting of carriers, excipients, vehicles, lipid dispersants, detergents, bile acid salts, and suspending, emulsifying, stabilizing, thickening, buffering, preserving, coloring, disintegrating, solubilizing, flavoring and sweetening agents.

32. The anti-atherogenic, anti-diarrheal, digestion, dissolution and/or absorption promoting and/or gastrointestinal transit slowing composition of claim 31, wherein the carriers are selected from the group consisting of solid, semisolid or liquid glucose, lactose, gum acacia, gelatin, mannitol, starch paste, magnesium trisilicate, talc, corn starch, keratin, colloidal silica, potato starch, urea, medium chain length triglycerides and dextrans.

33. A lipid dispersion, comprising the anti-diarrheal, anti-atherogenic, digestion, dissolution and/or absorption promoting, and/or gastrointestinal transit slowing composition of claim 31, and a lipid dispersant comprising an aqueous solution of an agent selected from the group consisting of at least one bile salt, at least one agent alkaline buffer and a detergent.

34. A lipid emulsion, comprising the anti-atherogenic, anti-diarrheal, digestion, dissolution and/or absorption promoting, and/or gastrointestinal transit slowing composition of claim 31, and a lipid dispersant comprising an agent which in the presence of the active lipid forms a two-phase emulsion.

35. A lipid suspension, comprising the anti-atherogenic, anti-diarrheal, digestion, dissolution and/or absorption promoting and/or gastrointestinal transit slowing composition of claim 31, and a lipid comprising a solid agent which forms a suspension with the active lipid.

36. An emulsion, comprising the anti-atherogenic, anti-diarrheal, digestion, dissolution and/or absorption promoting and/or gastrointestinal transit slowing composition of claim 31, emulsifiers and suspending agents; the emulsifiers and suspending agents being selected from the group consisting of gum acacia, agar, sodium alginates, bentonites, carbomers, celluloses, carrageenan, carboxymethyl celluloses, cholesterol, gelatins, octoxynol 9, oleyl alcohols, polyvinyl alcohols, povidone, propylene glycol monostearates, sodium lauryl sulfate, sorbitan esters, stearyl alcohol, tragacanth, xantham gum, chondrus, glycerin, trolamine, coconut oil, propylene glycol, ethyl alcohol, malt, malt extracts and mixtures thereof.

37. A cellulose emulsion, comprising the emulsion of claim 36, and celluloses which are selected from the group consisting of cellulose, hydroxyethyl celluloses, hydroxypropyl celluloses, hydroxypropyl methylcelluloses, methylcelluloses and mixtures thereof.

38. An oral formulation, comprising the anti-atherogenic, anti-diarrheal, digestion, dissolution and/or absorption promoting and/or gastrointestinal transit slowing composition of claim 27, and an oral carrier.

39. The oral formulation of claim 38, being in a form selected from the group consisting of capsules, coated and uncoated microspheres and particles, which may be encapsulated, tablets, troches, lozenges, aqueous and oily suspensions, dispersible powders and granules, emulsions, hard and soft capsules, syrups and elixirs.

40. A controlled release formulation, comprising the anti-atherogenic, anti-diarrheal, digestion, dissolution and/or absorption promoting, and/or gastrointestinal transit slowing composition of claim 27, and a controlled release coating.

41. A slow release formulation comprising the anti-atherogenic, anti-diarrheal, digestion, dissolution and/or absorption promoting, and/or gastrointestinal transit slowing composition of claim 27 and a slow release coating.

42. A liquid enteric formulation comprising the anti-atherogenic, anti-diarrheal, digestion, dissolution and/or absorption promoting, and/or gastrointestinal transit slowing composition of claim 27.

43. The liquid enteric formulation of claim 42, wherein the active ingredient comprises a dispersion of essential nutrients, pharmacological agents or mixtures thereof.

44. A method of prolonging small intestine transit time while promoting an anti-atherogenic and/or anti-diarrheal effect and/or promoting digestion, dissolution and/or absorption, comprising administering to a subject in need of treatment the composition of claim 27, wherein the active lipid is absorbed through the proximal segment of the small intestine in undegraded form and, thereby, increases small intestine transit time and produces an anti-atherogenic, anti-diarrheal, digestion, dissolution and/or absorption promoting and/or gastrointestinal transit slowing effect.

45. The method of claim 44, wherein the substance comprises nutrients.

46. The anti-atherogenic, anti-diarrheal, digestion, dissolution and/or absorption promoting and/or gastrointestinal transit slowing composition of claim 27, wherein the active lipid is selected from the group consisting of ($C_4$ to $C_{24}$) fatty acids and mixtures thereof.

47. The anti-atherogenic, anti-diarrheal, digestion, dissolution and/or absorption promoting and/or gastrointestinal transit slowing composition of claim 46, wherein the fatty acids are selected from the group consisting of caprolic acid, caprulic acid, capric acid, lauric acid, myristic acid, oleic acid, palmitic acid, stearic acid, palmitoleic acid, linoleic acid, linolenic acid, trans-hexadecanoic acid, elaidic acid, columbinic acid, arachidic acid, behenic acid, eicosenoic acid, erucic acid, bressidic acid, cetoleic acid, nervonic acid, Mead acid, arachidonic acid, timnodonic acid, clupanodonic acid, docosahexaenoic acid and mixtures thereof.

48. The method of claim 44, wherein the of active lipid triggers at least one reflex selected from the group consisting of intestino-lower esophageal sphincter or relaxation of LES reflex, intestino-gastric feedback or inhibition of gastric emptying reflex, intestino-intestinal feedback or ileo-jejunal feedback/ileal brake reflex, jejuno-jejunal feedback/jejunal brake reflex, intestino-CNS feedback or satiety intensifying intestinal signaling reflex, intestino-pancreatic feedback or exocrine enzyme output control reflex, intestino-biliary feedback or bile flow control reflex, intestino-mesenteric blood flow feedback reflex for mucosal hyperemia control and intestine-colonic feedback, gastro-colonic reflex or colon contracting response to nutrients, in the proximal segment of the small intestine.

49. A method of treating a nutritional deficiency comprising administering to a subject afflicted with a nutritional deficiency the anti-atherogenic, anti-diarrheal, digestion, dissolution and/or absorption promoting and/or gastrointestinal transit slowing composition of claim 29, in an amount and in a form effective to deliver the active lipid to the subject's proximal segment of the small intestine and, thereby, increase absorption of nutrients through the subject's small intestine.

50. The method of claim 49, wherein the subject's nutritional deficiency is associated with gastrointestinal symptoms selected from the group consisting of rapid intestinal transit, dumping syndrome, diarrhea, weight loss, distention, steatorrhea, asthenia and symptoms of specific nutrient deficiencies.

51. The method of claim 49, wherein the subject's nutritional deficiency is associated with a gastrointestinal disorder selected from the group consisting of post-gastrectomy syndrome, dumping syndrome, AIDS-associated chronic diarrhea, diabetes-associated diarrhea, post-vagotomy diarrhea, bariatrics surgery-associated diarrhea, short bowel syndrome, tube-feeding related diarrhea, chronic secretory diarrhea, carcinoid syndrome-associated diarrhea, gastrointestinal peptide tumors, endocrine tumors, chronic diarrhea associated with thyroid disorders, chronic diarrhea associated with bacterial overgrowth, chronic diarrhea in gastronomy, choleraic diarrhea, chronic diarrhea associated with giardiasis, antibiotic-associated chronic diarrhea, diarrhea-predominant irritable bowel syndrome, chronic diarrhea associated with maldigestion and malabsorption, chronic diarrhea associated with idiopathic primary gastrointestinal motility disorders, chronic diarrhea associated with collagenous colitis, surgery-associated acute diarrhea, antibiotic-associated acute diarrhea and infection-associated acute infectious diarrhea.

52. The method of claim 51, wherein the bariatrics surgery-associated diarrhea comprises obesity surgeries selected from the group consisting of gastric bypass, gastroplasties and intestinal bypass.

53. The method of claim 51, wherein the short bowel syndrome is selected from the group consisting of including resection of the small intestine after trauma, radiation induced complications, Crohn's disease and infarction of the intestine associated with vascular occlusion.

54. The method of claim 1, wherein the active lipid is administered in an amount of about 0.5 to about 2.0 g/dose.

55. The method of claim 12, wherein the active lipid is administered in an amount of about 0.5 to about 2.0 g/dose.

56. The method of claim 15, wherein the active lipid is administered in an amount of about 0.5 to about 2.0 g/dose.

57. The method of claim 16, wherein the active lipid is administered in an amount of about 0.5 to about 2.0 g/dose.

58. The method of claim 17, wherein the active lipid is administered in an amount of about 0.5 to about 2.0 g/dose.

59. The method of claim 19, wherein the active lipid is administered in an amount of about 0.5 to about 2.0 g/dose.

60. The method of claim 25, wherein the active lipid is administered in an amount of about 0.5 to about 2.0 g/dose.

61. The method of claim 26, wherein the active lipid is administered in an amount of about 0.5 to about 2.0 g/dose.

62. The method of claim 44, wherein the active lipid is administered in an amount of about 0.5 to about 2.0 g/dose.

63. The method of claim 49, wherein the active lipid is administered in an amount of about 0.5 to about 2.0 g/dose.

\* \* \* \* \*

UNITED STATES PATENT AND TRADEMARK OFFICE
CERTIFICATE OF CORRECTION

PATENT NO. : 5,977,175
DATED : Nov. 2, 1999
INVENTOR(S) : Henry C. Lin

It is certified that error appears in the above-identified patent and that said Letters Patent is hereby corrected as shown below:

At column 14, lines 19-20, Claim 1, change "substance dissolution, bioavailability and/or through" to --substance's dissolution and/or bioavailability through--.

At column 14, line 22, Claim 1, change "there through" to --therethrough--.

At column 14, line 56, Claim 10, insert a comma between "behenic acid" and "eicosenoic acid".

At column 16, line 47, Claim 25, change "anti-atherogenes" to --anti-atherogenesis--.

At column 17, line 37, Claim 30, insert a comma between "antiatherogenic" and "anti-diarrheal".

At column 19, line 14, Claim 48, change "wherein the of active lipid" to --wherein the active lipid--.

Signed and Sealed this

Twenty-fourth Day of October, 2000

Q. TODD DICKINSON

*Attest:*

*Attesting Officer*  *Director of Patents and Trademarks*

UNITED STATES PATENT AND TRADEMARK OFFICE
CERTIFICATE OF CORRECTION

| | | |
|---|---|---|
| PATENT NO. | : 5,977,175 | Page 1 of 1 |
| APPLICATION NO. | : 08/832307 | |
| DATED | : November 2, 1999 | |
| INVENTOR(S) | : Henry C. Lin et al. | |

It is certified that error appears in the above-identified patent and that said Letters Patent is hereby corrected as shown below:

In column 1, after the cross-reference to related applications but before the "Field of the Invention" section, please insert the following:

--FEDERAL SUPPORT
The U.S. Government has a paid-up license in this invention and the right in limited circumstances to require the patent owner to license others on reasonable terms as provided for by the terms of Grant Nos. DK059983 and DK046459 awarded by the National Institutes of Health.--

Signed and Sealed this
Twenty-second Day of January, 2013

David J. Kappos
*Director of the United States Patent and Trademark Office*